United States Patent [19]

Kinameri

[11] Patent Number: 4,702,607
[45] Date of Patent: Oct. 27, 1987

[54] THREE-DIMENSIONAL STRUCTURE VIEWER AND METHOD OF VIEWING THREE-DIMENSIONAL STRUCTURE

[75] Inventor: Kanji Kinameri, Nishitama, Japan

[73] Assignee: Hitachi, Ltd., Tokyo, Japan

[21] Appl. No.: 807,686

[22] Filed: Dec. 11, 1985

[30] Foreign Application Priority Data

Dec. 14, 1984 [JP] Japan ................................ 59-262778

[51] Int. Cl.$^4$ ........................................... G01N 21/00
[52] U.S. Cl. ...................................... 356/432; 356/435
[58] Field of Search ......... 356/432, 435, 436, 440–441, 356/237

[56] References Cited

U.S. PATENT DOCUMENTS 3,013,467 12/1961 Minsky ................................. 356/432

FOREIGN PATENT DOCUMENTS 1063618 6/1959 France ................................. 356/435

Primary Examiner—R. A. Rosenberger
Assistant Examiner—Crystal D. Cooper
Attorney, Agent, or Firm—Antonelli, Terry & Wands

[57] ABSTRACT

The present invention relates to viewing a three-dimensional internal structure of a specimen. According to the invention, it is possible to observe the internal structure of a particular cross section of a specimen as clearly differentiated from the other cross sections. The characteristic features of the invention lie in that a plurality of light beams passing through different portions inside the specimen are used, and a correlation among the measurements of transmittance of the plurality of light beams is determined.

20 Claims, 4 Drawing Figures

THREE-DIMENSIONAL STRUCTURE VIEWER AND METHOD OF VIEWING THREE-DIMENSIONAL STRUCTURE

BACKGROUND OF THE INVENTION

The present invention relates to an apparatus for inspecting the internal structure of a specimen by detecting the strength of a light beam transmitted through the specimen, and more particularly to a three-dimensional structure viewer for inspecting the three-dimensional internal structure of the specimen, i.e., discovering the presence of, for example, defects in a particular cross-section thereof.

To observe the three-dimensional structure of a specimen, there has hitherto been proposed one method which uses a confocal microscope. The basic principal of this method is discussed in a document entitled "Three-Dimensional Surface Measurement Using the Confocal Scanning Microscope" by Hamilton and Wilson in Appl. Phys. B 27.211 (1982).

One example of an arrangement of the basic principle of a conventional three-dimensional structure viewer using a confocal microscope is shown in FIG. 1. In FIG. 1, a parallel light beam 2 emitted from a light source 1, e.g., a laser generator, is made to be incident upon a lens 4 through, for instance, a mirror 3 so as to cause the light beam to converge at a point 6 within a specimen 5. The light beam which is transmitted through the specimen 5 is made to converge again at the position of a pinhole 8 by a lens 7. The light beam which is transmitted through the pinhole 8 is made to be incident upon a photodetector 9, and the strength thereof is converted into an electrical signal. The electrical signal issued by the photodetector 9 is amplified by, for instance, an amplifier 10, and is then transfered as a video signal to an image display 11. Meanwhile, the specimen 5 is scanned by specimen scanners 12 and 13 with respect to the planes thereof which are parallel with the surface of the specimen 5. These scanning signals are transfered to the scanning controllers 14 and 15 of the image display 11, which in turn displays the distribution of the transmitted light beam in a case where the specimen 5 is scanned, as, for instance, monochromatic images.

In this case, the image display 11 displays the transmittance distribution within a cross-section parallel with the surface of the specimen, including a convergent point 6, by virtue of the effect of the confocal microscope using the pinhole 8. Accordingly, it becomes possible to observe the three-dimensional internal structure of the specimen 5 by varying the relative position of the convergent point inside the specimen 5 by means of a specimen scanner 16 disposed vertically with respect to the specimen's surface and by repeating the aforementioned operation. FIG. 2 shows an example of output signals of the photodetector 9 used in the apparatus shown in FIG. 1 in a case where semitransparent or opaque fine objects are present inside the specimen 5. With respect to fine objects 17 and 18 which are present in a cross-section including the convergent point of the light beam, video signals 17' and 18' corresponding to the transmittance thereof are obtained. With respect to fine objects 19, 20, 21, and 22 which are present in the other cross-sections, the strength of the transmitted light beam declines when these fine objects are located in the range of the light beam, with the result that such video signals as those shown at 19', 20', 21', and 22' are obtained. Consequently, if images are displayed using the signals of FIG. 2, there is a drawback in the sense that information on the other cross-sectional structures is superposed on the information as to fine objects 17 and 18 with respect to the desired cross-sectional structure, thereby making it difficult to effect observation of a three-dimensional structure in a true sense.

SUMMARY OF THE INVENTION

Accordingly, an object of the present invention is to provide a three-dimensional structure viewer and a method of viewing a three dimensional structure which are capable of observing information on the structure of a particular cross-section inside a specimen in such a manner as to clearly differentiate that information from that on the other cross-sections.

To attain the aforementioned object, the present invention is characterized in that a plurality of light beams passing through different portions within a specimen are used, and that the correlation of transmittance measurements is determined using these light beams. By virtue of this characteristic feature, it becomes possible to effect the observation of a three-dimensional structure in a particular cross-section as differentiated from the other cross-sections of the inside of a specimen.

DESCRIPTION OF THE PRESENT PREFERRED EMBODIMENTS

Figure 3:
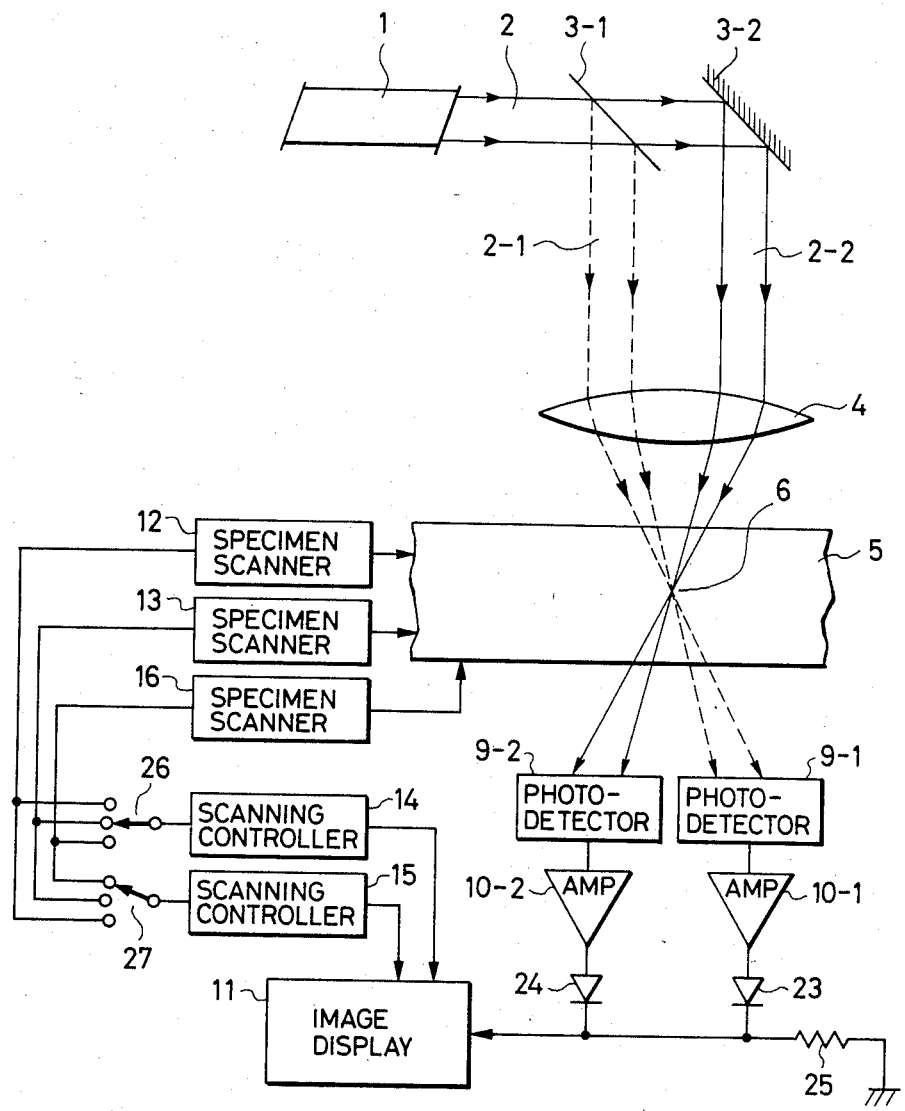
FIG. 3 is a schematic diagram of a three-dimensional structure viewer illustrating one embodiment of the present invention.

Description of the present invention will be made hereafter with reference to the attached drawings. FIG. 3 illustrates one embodiment of the present invention. In FIG. 3, a parallel light beam 2 is made to diverse into light beams 2-1 and 2-2 by means of, for instance, a half mirror 3-1 and a mirror 3-2. These light beams 2-1 and 2-2 are then made to be incident upon a lens 4, thereby causing both light beams to converge into an internal point 6 within the specimen 5. With respect to the light beams 2-1 and 2-2 which have passed through the specimen 5, their strength is converted into electrical signals by photodetectors 9-1 and 9-2, and these electrical signals are amplified by amplifiers 10-1 and 10-2. The outputs of the amplifiers 10-1 and 10-2 are sent to a maximum value detecting circuit constituted by diodes 23, 24 and a resistor 25. The maximum value of the light beam strength thus obtained is imparted to an image display as a video signal. Meanwhile, the specimen 5 is subjected to two-dimensional scanning by specimen scanners 12, 13, and 16 with respect to the planes thereof which are horizontal or vertical with respect to the surface of the specimen 5. In this case, it is also possible to scan the entire plurality of light beams, instead of scanning a specimen itself. These scanning signals are selected by switches 26 and 27, and are transmitted to the scanning controllers 14 and 15 of the image display 11. Consequently, the image display 11 displays, as, for instance monochromatic images, the variations in the maximum value of the strength of transmitted light beams in a case where the specimen 5 is scanned with respect to the planes thereof which are horizontal or vertical with respect to the surface of the specimen 5.

Figure 1:
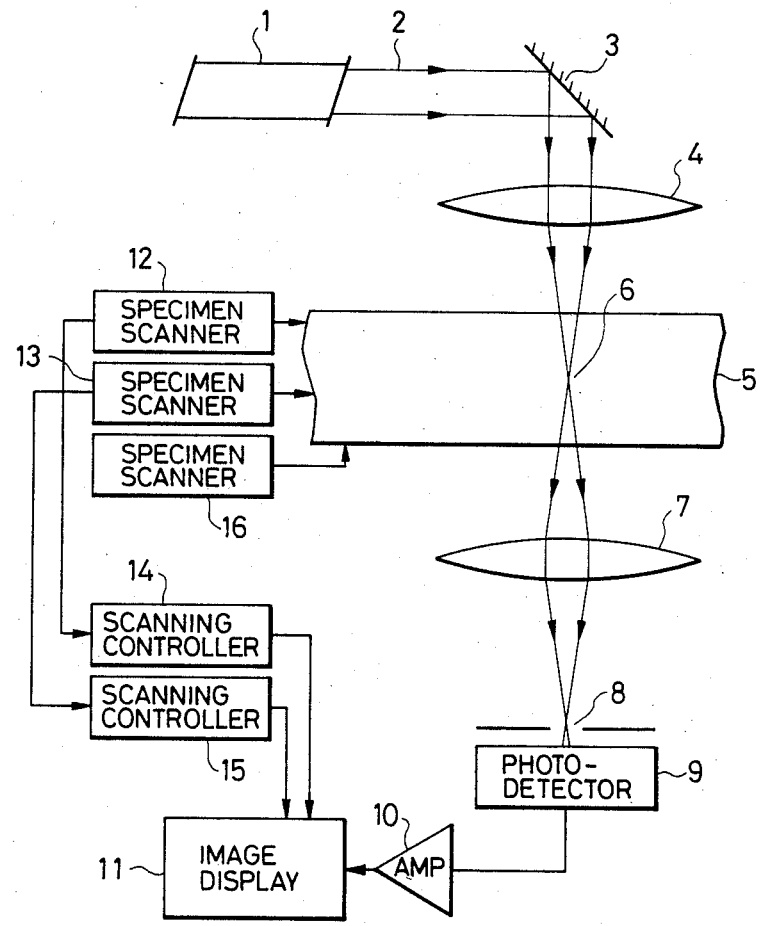
FIG. 1 is a schematic diagram of a three-dimensional structure viewer based on a conventional basic principal.
Figure 2:
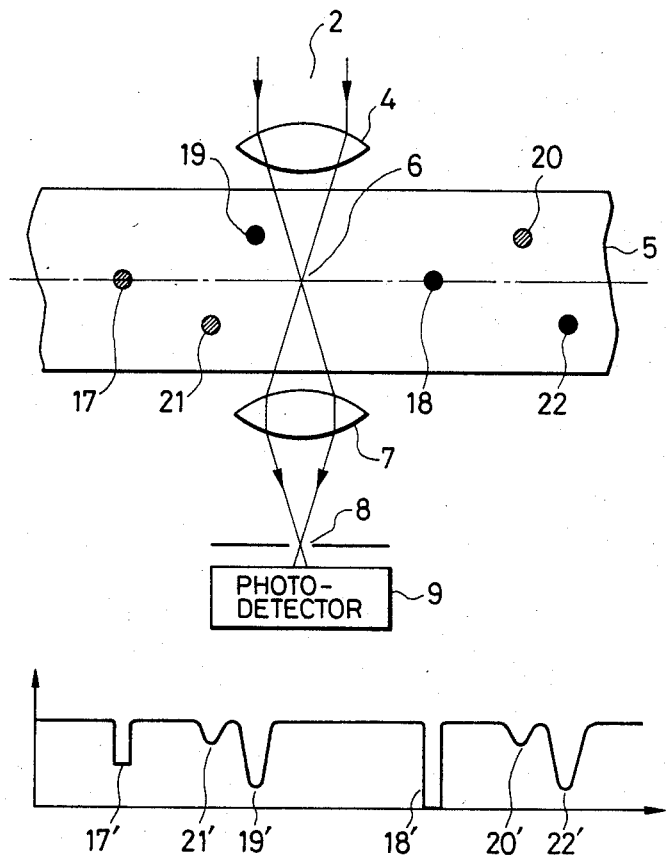
FIG. 2 is a diagram explaining the basic principle of a conventional method.
Figure 4:
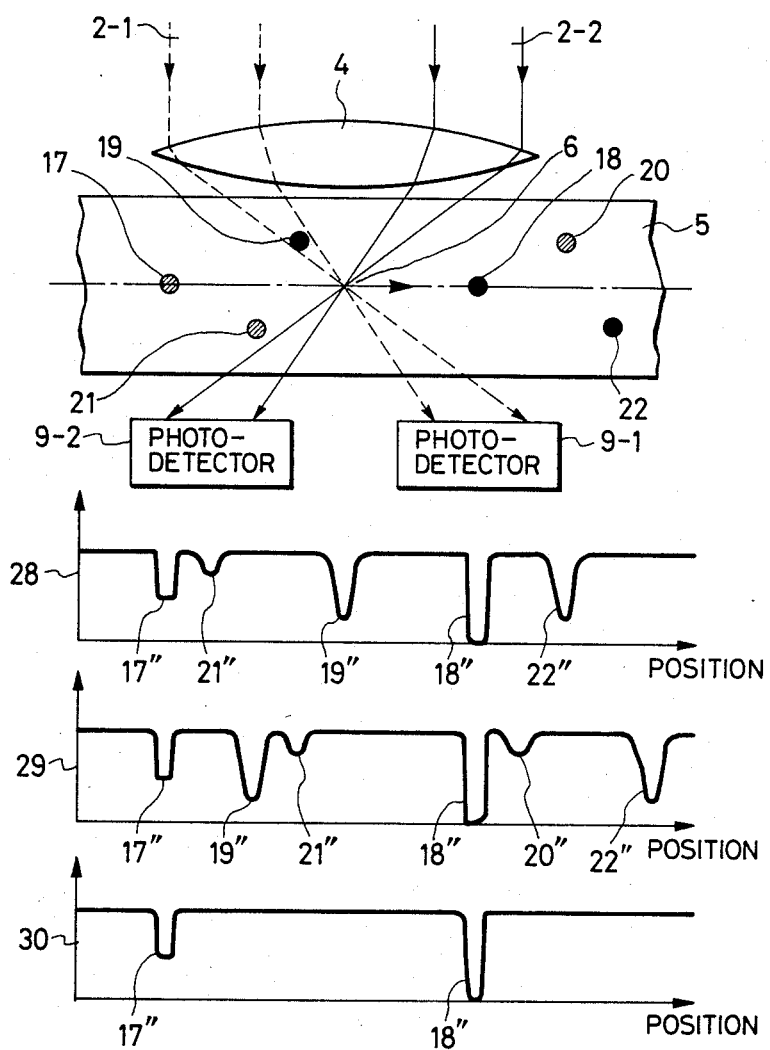
FIG. 4 is a diagram explaining the basic principle of the present invention.

In this case, by using the aforementioned maximum value as a video signal, the image display 11 displays transmittance distribution in cross-sections which are horizontal or vertical with respect to the surface of the specimen, including the convergent point 6. Consequently, it is possible to observe the three-dimensional internal structure of the specimen 5 by varying the relative position of a convergent point 6 within the specimen by means of the specimen scanners 12, 13, or 16 disposed vertically with respect to the scanning planes, and by repeating this two-dimensional scanning. FIG. 4 shows an example in which semitransparent and opaque fine objects are present in the specimen 5 under the same conditions as those of FIG. 2, and the plane including the convergent point 6 of the light beams is scanned in the direction of the arrow. FIG. 4 also shows the output signal waveform 28 of the photodetector 9-1 and the output signal waveform 29 of the photodetector 9-2 in the apparatus shown in FIG. 3, as well as the result of selecting either of the maximum signals of these waveforms 28 and 29 after amplifying them respectively, i.e., a video signal waveform 30 to be transmitted to the image display 11. In this case, with respect to the fine objects 17 and 18, output signals corresponding to the transmittance thereof are obtained by both photodetectors 9-1 and 9-2 as 17'' and 18'' at the same positions as those on the signal waveforms 28 and 29, respectively. Meanwhile, with respect to the fine objects 19, 20, 21, and 22 which are present in cross-sections other than that mentioned above, since the strength of the transmitted light beams declines when these fine objects are located such as to be included in cross-sections other than that including the convergent point of the light beams 2-1 and 2-2, these fine objects appear as the signals 19'', 20'', 21'', and 22'' in the output signal waveforms 28 and 29 of the photodetectors 9-1 and 9-2. In other words, the signals of the fine objects that are present in the desired cross-section appear in the same positions in the output signal waveforms of the photodetectors 9-1 and 9-2, while signals corresponding to the fine objects that are present in the other cross-sections appear in different positions when detected by the respective photodetectors. Accordingly, it is possible to take out only the signals of the fine objects that are present in the desired plane by determining a correlation between the two output signal waveforms. Specifically, if an attempt is made to find the maximum values of the outputs of the photodetectors 9-1 and 9-2, the signals become as shown in the signal waveform 30. Thus, as shown by the signals 17'' and 18'', it can be seen that only the signals of the fine objects that are present in the desired cross-section including the convergent point 6 have been taken out. In other words, if images are displayed using the signal waveform 30 of FIG. 4, it is possible to observe the structure of a desired cross-section.

The above-described embodiment is a case where two light beams are used. However, it is possible to effect a more positive inspection of a three-dimensional structure on the basis of a similar concept using any plurality of light beams, photodetectors and amplifiers corresponding to the respective light beams, and maximum value detecting circuits for the respective outputs.

The embodiment shown in FIG. 3 shows a case in which one light source is used, but two separate light sources may be used. As a light source, it is possible to use a laser generator, a light emitting diode, or a cathode-ray tube. When an object is a transparent specimen, a visible ray may be used. For instance, if the object is a silicon crystal, it is possible to observe a three-dimensional structure if a near ultrared ray with a wavelength of 0.8–1.2 $\mu$m is used. In addition, it is also possible to use a light source emitting an ultraviolet ray or ultrared ray.

As described above, according to the present invention, it is possible to easily and efficiently observe the structure of a particular cross-section in a transparent specimen.

We claim:

1. A three-dimensional structure viewer comprising: light beam generating means for generating a plurality of light beams; light beam applying means capable of applying said plurality of light beams so as to intersect one another at a desired convergent point within a specimen; transmitted light beam strength detecting means for individually detecting the strength of said respective light beams which have passed through said specimen; scanning means for scanning either said specimen or all of said plurality of light beams; and image displaying means for displaying as an image an output from said transmitted light beam strength detecting means synchronously with said scanning.

2. A three-dimensional structure viewer according to claim 1, wherein said scanning means is arranged so as to be capable of viewing a structure in a cross-section parallel to a surface of said specimen at a particular depth from said surface by means of two-dimensional scanning parallel to the surface of said specimen.

3. A three-dimensional structure viewer according to claim 2, wherein there is provided maximum value extracting means for finding a maximum value among the detected values of said plurality of light beams obtained by said transmitted light beam strength detecting means, and the output of said maximum value extracting means is displayed as an image by said image displaying means.

4. A three-dimensional structure viewer according to claim 3, wherein said light beam generating means for generating said plurality of light beams includes one laser beam source as well as a half mirror and a mirror which together divide the light beam from said laser beam source into two light beams.

5. A three-dimensional structure viewer according to claim 3, wherein said light beam applying means is an optical system which converges said plurality of light beams onto a point within said specimen.

6. A three-dimensional structure viewer according to claim 3, wherein said maximum value extracting means comprises means for amplifying the output from said transmitted light beam strength detecting means, and a diode and a resistor connected to said amplifying means.

7. A three-dimensional structure viewer according to claim 1, wherein said scanning means is arranged so as to be capable of viewing a structure in a particular cross-section perpendicular to a surface of said specimen by means of two dimensional scanning perpendicular to said surface.

8. A three-dimensional structure viewer according to claim 7, wherein there is provided maximum value extracting means for finding a maximum value among the detected values of said plurality of light beams obtained by said transmitted light beam strength detecting means, and the output of said maximum value extracting means is displayed as an image by said image displaying means.

9. A three-dimensional structure viewer according to claim 8, wherein said light beam generating means for generating said plurality of light beams includes one laser beam source as well as a half mirror which divides the light beam from said laser beam source into two light beams.

10. A three-dimensional structure viewer according to claim 8, wherein said light beam applying means is an optical system which converges said plurality of light beams into a point within said specimen.

11. A three-dimensional structure viewer according to claim 8, wherein said maximum value extracting means comprises means for amplifying the output from said transmitted light beam strength detecting means, and a diode and a resistor connected to said amplifying means.

12. A three-dimensional structure viewer comprising:
light beam generating means for generating a plurality of light beams;
light beam applying means capable of applying said plurality of light beams so as to intersect one another at a desired convergent point within a specimen;
transmitted light beam strength detecting means for individually detecting the strength of said respective light beams which have passed through said specimen;
means for extracting the detected value of a light beam strength when light beam strength components of each detected light beam vary simultaneously;
scanning means for scanning either said specimen or all of said plurality of light beams; and
image displaying means for displaying as an image an output from said transmitted light beam strength detecting means synchronously with said scanning.

13. A three-dimensional structure viewer according to claim 12, wherein said scanning means is arranged so as to be capable of viewing a structure in a cross-section parallel to a surface of said specimen at a particular depth from said surface by means of a two-dimensional scanning parallel to said surface of said specimen.

14. A three-dimensional structure viewer according to claim 13, wherein said light beam generating means for generating said plurality of light beams includes one laser beam source as well as a half mirror and a mirror which together divide the light beam from said laser beam source into two light beams.

15. A three-dimensional structure viewer according to claim 13, wherein said light beam applying means is an optical system which converges said plurality of light beams into a point within said specimen.

16. A three-dimensional structure viewer according to claim 12, wherein said scanning means is arranged so as to be capable of viewing a structure in a particular cross-section perpendicular to a surface of said specimen by means of two-dimensional scanning perpendicular to the surface of said specimen.

17. A three-dimensional structure viewer according to claim 16, wherein said light beam generating means for generating said plurality of light beams includes one laser beam source as well as a half mirror and a mirror which together divide the light beam from said laser beam source into two light beams.

18. A three-dimensional structure viewer according to claim 16, wherein said light beam applying means is an optical system which converges said plurality of light beams onto a point within said specimen.

19. A method of viewing a three-dimensional structure of the inside of a specimen comprising the steps of: generating a plurality of light beams; applying said plurality of light beams so as to intersect one another at a desired convergent point within a specimen; scanning either said specimen or all of said plurality of light beams; individually detecting the strength of said plurality of transmitted light beams which have been transmitted through said specimen; and displaying as a video image an output of said transmitted light beam strength synchronously with said scanning.

20. A method of viewing a three-dimensional structure according to claim 19, wherein the maximum strength of said plurality of transmitted light beams is found, and said maximum transmitted beam strength is displayed as an image synchronously with said scanning.

* * * * *